United States Patent [19]

Mukherjee et al.

[11] Patent Number: 4,808,351
[45] Date of Patent: Feb. 28, 1989

[54] PROCESS FOR MANUFACTURING A MOLDED PROSTHETIC DEVICE

[75] Inventors: Debi P. Mukherjee, Brookfield, Conn.; Kurt A. Feichtinger, Ringwood, N.J.

[73] Assignee: American Cyanamid Company, Stamford, Conn.

[21] Appl. No.: 715,547

[22] Filed: Mar. 25, 1985

[51] Int. Cl.$^4$ .................. B29C 45/00; B29C 71/02
[52] U.S. Cl. .................... 264/22; 264/83; 264/328.16; 264/331.21; 264/346; 264/235
[58] Field of Search ......... 128/92 BC, 334 R, 334 C; 623/1, 11, 16; 264/346, 235, 222, 221, 223, 328.5, 328.1, 234, 328.15, 328.16, 331.21, 345, 334, 22, 83; 528/272, 300

[56] References Cited

U.S. PATENT DOCUMENTS

| | | | |
|---|---|---|---|
| 3,422,181 | 1/1969 | Chirgwin | 264/346 X |
| 3,483,287 | 12/1969 | Davis | 264/328.5 X |
| 3,516,957 | 6/1970 | Gray, Jr. et al. | |
| 3,565,869 | 2/1971 | De Prospero | 264/331.21 X |
| 3,620,218 | 11/1971 | Schmitt et al. | 128/334 R |
| 3,626,948 | 12/1971 | Glick et al. | 128/335.5 |
| 3,739,773 | 6/1973 | Schmitt et al. | 128/92 BC |
| 3,772,420 | 11/1973 | Glick et al. | 264/345 X |
| 3,878,284 | 4/1975 | Schmitt et al. | 264/331.21 X |
| 3,890,283 | 6/1975 | Casey et al. | |
| 4,042,978 | 8/1977 | Jones et al. | 623/1 X |
| 4,264,558 | 4/1981 | Jacobsen | 264/523 |
| 4,341,875 | 7/1982 | Visger et al. | 264/328.1 X |
| 4,387,815 | 6/1983 | Jacobsen | 215/1 C |
| 4,404,161 | 9/1983 | Bier | 264/328.16 |
| 4,485,134 | 11/1984 | Jacobsen | 428/35 |
| 4,490,326 | 12/1984 | Beroff et al. | 264/328.16 |
| 4,496,446 | 1/1985 | Ritter et al. | 264/22 X |
| 4,523,591 | 6/1985 | Kaplan et al. | 128/334 R |
| 4,534,003 | 8/1985 | Manzione | 264/328.1 X |

FOREIGN PATENT DOCUMENTS 199074 10/1986 European Pat. Off. .

OTHER PUBLICATIONS

Mandelkern, L. Crystallization of Polymers, New York, McGraw-Hill Book Co., 1964, pp. 215–224.
"Crystallinity", In: Encyclopedia of Polymer Science and Technology (John Wiley & Sons, 1966), p. 462.
"Kinetics of Crystallization", In: Encyclopedia of Polymer Science and Technology (John Wiley & Sons, 1968), p. 63.
Glanvill, A. B. "Injection Molding", In: Thermoplastics: Effects of Processing (Cleveland, CRC Press, 1969), pp. 127–135.
Gilding, D. K. et al. "Biodegradable Polymers for Use in Surgery–Polyglycolic/Poly(Actic Acid) Homo–and Copolymers:1", Polymer, vol. 20 (Dec. 1979), pp. 1459–1464.

Primary Examiner—Jan H. Silbaugh
Assistant Examiner—Leo B. Tentoni
Attorney, Agent, or Firm—Charles F. Costello, Jr.

[57] ABSTRACT

An improved process for manufacturing a molded prosthetic device from a synthetic bioabsorbable polymer is disclosed. The process includes placing a solid amount of the polymer in a molding machine; melting the polymer by subjecting it to a temperature of from about 240° to 255° C. for about 2 to 5 minutes; transporting the polymer melt to an orifice; injecting the polymer melt from the orifice into a closed mold cavity at a pressure of from about 8000 to 9000 lbs per square inch (562 to 633 kg per sq. cm.); holding the polymer in the mold cavity for less than about one minute at a temperature of about 70° to 90° C.; removing a molded prosthetic device from the mold cavity; and posttreating the molded prosthetic device. The posttreating can be, e.g., annealing and then/or sterilizing.

4 Claims, No Drawings

PROCESS FOR MANUFACTURING A MOLDED PROSTHETIC DEVICE

FIELD OF THE INVENTION

This invention relates to an improved process for manufacturing a molded prosthetic device. More specifically, this invention relates to an improved process for manufacturing a posttreated molded prosthetic device from a synthetic bioabsorbable polymer. The posttreating can be, e.g., annealing and then/or sterilizing.

SUMMARY AND DESCRIPTION OF THE INVENTION

An improved process for manufacturing a molded prosthetic device from a synthetic bioabsorbable polymer has been invented. The process comprises placing a solid amount of the polymer in a molding machine; melting the polymer by subjecting it to a temperature of from about 240° to 255° C. for about 2 to 5 minutes; transporting the polymer melt to an orifice; injecting the polymer melt from the orifice into a closed mold cavity at a pressure of from about 8000 to 9000 lbs per square inch (562 to 633 kg. per sq. cm.); holding the polymer in the mold cavity for less than about one minute at a temperature of about 70° to 90° C.; removing a molded prosthetic device from the mold cavity; and posttreating the molded prosthetic device. The posttreating step can be, e.g., annealing and then/or sterilizing.

With the posttreating step, one embodiment is wherein the polymer contains a glycolic acid ester linkage. In a more specific embodiment, the polymer is a homopolymer. In another more specific embodiment, the polymer is a copolymer.

Another embodiment with the posttreating step is wherein the molding machine is an injection or blow or compression molding machine. In a more specific embodiment, the compression machine is a transfer molding machine.

Yet another embodiment with the posttreating step is wherein the melting of the solid polymer is at a temperature of about 250° C. Still another embodiment is wherein the orifice has a temperature of about 240° C. Further, another embodiment is wherein the injecting of the polymer melt is at a pressure of about 9000 lbs per square inch (633 kg/sq. cm). Finally, other embodiments are wherein the maximum thickness of the polymer in the mold cavity is about 0.25 inches; wherein the holding of the polymer in the mold cavity is from about 20 to 30 seconds; and wherein the holding of the polymer is at a temperature of about 90° C.

With the posttreating step being sterilizing, one embodiment is wherein the polymer is a homopolymer. Another embodiment is wherein the orifice has a temperature of about 240° C. A further embodiment is wherein the maximum thickness of the polymer in the mold cavity is about 0.25 inch.

With the posttreating step being annealing, one embodiment comprises annealing and then sterilizing the molded prosthetic device. In another embodiment, the annealing is at a temperature of at least about 110° C. under a vacuum of at least about 755 mm of Hg. In a more specific embodiment, the annealing is at about 110° C. under a vacuum of at least about 757 mm of Hg for about 2 to 3 hours.

I. Higher Mold Temperature To Reduce Dimensional Changes Of Molded Devices Encountered During Annealing Standard ASTM 2½"×½"×⅛" flexural test samples were injection molded from PGA on an Arburg molding machine using various mold temperatures from 87° F. up to 194° F. Green strength and flexural (3 point bending) properties were measured, that is parts immediately removed from the machine. Flexural (3 point bending) properties as well as mold shrinkage were measured on "as-molded" parts after room temperature cooling. Shrinkage during annealing was determined from linear dimensional measurements taken both before and after annealing. Flexural (3 point bending) properties were also determined on the annealed samples. Specific details on the test procedures and results may be found in the tables.

The following terms are used in Tables 1 to 6:

A. Green Properties: Modulus and strength properties increased with mold temperature up to approximately 120° F. mold temperature, then stabilized at a lower value for mold temperatures from 140° F. to 194° F.

B. Linear Mold Shrinkage: Shrinkage dropped with increasing mold temperatures to a minimum at mold temperature of approximately 120° F. then increased slightly as the mold temperature was increased to 194° F.

C. "As molded" Flexural Properties: Modulus and strength properties increased by about 10% for mold temperatures above 180° F. Ultimate strain, which is a measure of ductility, uniformly increased with mold temperature. Thus, samples using a mold temperature above 180° F. were tougher, stronger and stiffer than those molded at 100° F. which is currently used to mold BAR devices.

D. Shrinkage During Annealing: The linear shrinkage which occurred during annealing for samples using mold temperatures above approximately 160° F. was very low and less than the experimental error associated with the measurement.

E. Annealed Flexural Properties: The flexural (3 point bending) properties on annealed samples did not change with mold temperature.

Recommendations:

A. "Hot" molds (above 180° F.) should be employed when molding PGA where dimensional stability during annealing is desired.

B. Temperature control is crucial to part yield. An adequate controller is therefore required which can achieve this level of control.

Results And Discussion

The green properties of ultimate strength and flexural modulus increased with mold temperature, reaching a peak value at a mold temperature of 116° F. after which they dropped somewhat. Ultimate strain increased uniformly with increasing mold temperature. The linear shrinkage reached a minimum value at a mold temperature of approximately 116° F. Since the Tg of PGA is around 104° F. these observations are somewhat related to glass transition behavior.

The flexural and ultimate properties of "as-molded" parts did not show any change until the mold temperature was increased above approximately 181° F. When the higher mold temperature samples were annealed, these properties did not change appreciably. However, the shrinkage during annealing of parts molded with mold temperatures higher than 158° F. was very low and within the range of the experimental error. These results are caused by a complex interaction of rates of cooling and crystallization at temperatures higher and lower than the glass temperature which is around 104° F. for PGA. Additional differential scanning colorimeter work may give more insight into the mechanism of these changes.

However, these changes indicate that higher mold temperatures will yield devices with a negligible degree of shrinkage during annealing. Therefore, higher mold temperatures are recommended to reduce shrinkage and possibly warpage of devices during annealing.

The results of part I are shown in the following Tables 1 to 6.

TABLE 1

Process Details

A. Materials: PGA, 1.34 I.V.
B. Equipment:
  (1) 40 ton Clamp Arburg Model #220 - 90 - 350 (Serial #118072) with 25 mm screw, nylon-type nozzle with negative taper, 1.55 oz. shot size.
  (2) ASTM Mold #5129 with 2½" × ½" × ⅛" flexural sample, end-gated.
C. Processing Parameters
  Temperatures:
  | | |
  |---|---|
  | Feed Throat: | city water chilled |
  | Zone 1: | 490° F. (255° C.) |
  | Zone 2: | 475° F. |
  | Zone 3: | 475° F. |
  | Zone 4: (Nozzle) | 470° F. (243° C.) |

Pressures*/Times:
  | | |
  |---|---|
  | Initial Inject: | 8200 psi/3.5 sec. |
  | Holding: | 3280 psi/1.4 sec. |
  | Back: | None |
  | Mold Cure: | 20.0 sec. |
  | Overall Cycle: | 34 sec. |

Screw Speed: 50–70 rpm
  *Specific Pressure
D. Samples: approximately 25 samples each at 87, 102, 116, 140, 158, 181 and 194° F. mold temperatures (measured) were collected. Five each were measured immediately out of the mold for flexural 3-point bending properties. Five each were annealed at 110° C. under vacuum for 3 hrs. The results are shown in Tables I to V below.

TABLE 2

PGA GREEN PROPERTIES IN FLEXURAL 3-POINT BENDING

Green Properties: samples immediately removed from the machine were degated and tested in flexure for three-point bending performance. A 2" span was used with 5 in/min crosshead and 50 in/min chart speeds to minimize cooling effects. A 20 lb. full scale range was used. Calculations for modulus, ultimate strength and strain follow ASTM #D-790 procedures. The results are as shown below.

| | MOLD TEMPERATURE* | | | | | | |
|---|---|---|---|---|---|---|---|
| | 87° F. | 102° F. | 116° F. | 140° F. | 158° F | 181° F. | 194° F. |
| Flexural Modulus, (psi) | 119,000 ±16,000 | 130,000 ±9,330 | 159,000 ±10,100 | 118,000 ±9,050 | 104,000 ±5,140 | 112,000 ±10,000 | 106,000 ±4,180 |
| Ultimate Strength, (psi) | 6,190 ±590 | 6,520 ±419 | 7,900 ±323 | 6,550 ±168 | 6,320 ±327 | 6,260 ±230 | 6,230 ±111 |
| Ultimate Strain, (%)** | 8.64 ±0.20 | 8.99 ±0.23 | 9.22 ±0.06 | 9.04 ±0.30 | 9.04 ±0.51 | 9.24 ±0.08 | 9.32 ±0.32 |

NOTES:
Samples removed immediately from machine, degated and tested.
2" span
5 in/min. crosshead speed
50 in/min. chart speed
20 lb. full scale range
ASTM #D-790 procedure
*Measured
**Calculated strains much greater than 5–6% are no accurate due to inability to locate neutral axis.

TABLE 3

PGA LINEAR MOLD SHRINKAGE

Linear Mold Shrinkage: Using the 2½" length, average of each side of the gate, the ASTM #D-955 procedure was used to calculate mold shrinkage.

$$\text{Mold-Shrinkage (in/in)} = \frac{\text{Mold Cavity Dimension} - \text{Specimen Dimension}}{\text{Mold Cavity Dimension}}$$

| | MOLD TEMPERATURE* | | | | | | |
|---|---|---|---|---|---|---|---|
| | 87° F. | 102° F. | 116° F. | 140° F. | 158° F. | 181° F. | 194° F. |
| Linear Mold Shrinkage, (in/in) | 0.0234 ± 0.0005 | 0.0210 ± 0.0013 | 0.0186 ± 0.0015 | 0.0205 ± 0.0009 | 0.0209 ± 0.010 | 0.0226 ± 0.0010 | 0.0214 ± 0.0004 |

NOTES:
Shrinkage in 2½" length dimension, average of lengths on right and left side of gate ASTM #D-955 procedure $$\text{Linear Mold Shrinkage (in/in)} = \frac{\text{Mold Cavity Dimension} - \text{Specimen Dimension}}{\text{Mold Cavity Dimension}}$$

*Measured

TABLE 4

PGA "AS MOLDED" PROPERTIES IN FLEXURAL 3-POINT BENDING

"As-Molded" Flexural Properties: samples which had cooled overnight in the dry locker were tested in flexure for three-point bending performance. A 2" span was used with 0.2 in/min crosshead and 5.0 in/min chart speeds. A 100 lb. full scale range was used. Calculations for modulus, ultimate strength and strain followed ASTM #D-790 procedures.

| | MOLD TEMPERATURE* | | | | | | |
|---|---|---|---|---|---|---|---|
| | 87° F. | 102° F. | 116° F. | 140° F. | 158° F. | 181° F. | 194° F. |
| Flexural Modulus, (psi) | $1.03 \times 10^6$ ±21,500 | $1.02 \times 10^6$ ±21,700 | $1.04 \times 10^6$ ±14,800 | $1.05 \times 10^6$ ±16,300 | $1.08 \times 10^6$ ±27,700 | $1.14 \times 10^6$ ±17,200 | $1.14 \times 10^6$ ±27,900 |
| Ultimate Strength, (psi) | 30,200 ±372 | 30,800 ±2,330 | 29,700 ±853 | 30,700 ±258 | 31,800 ±521 | 33,100 ±260 | 32,800 ±253 |
| Ultimate Strain, (%) | 4.40 ±0.12 | 4.56 ±0.12 | 4.62 ±0.25 | 5.17 ±0.08 | 5.13 ±0.13 | 5.24 ±0.10 | 5.35 ±0.12 |

NOTES:
Molded samples allowed to cool overnight in dry locker prior to testing.
2" span
0.2 in/min. crosshead speed
5.0 in/min. chart speed
100 lb. full scale range
ASTM #D-790 procedure
*Measured

TABLE 5

PGA LINEAR SHRINKAGE DURING ANNEALING

Shrinkage During Annealing: Similar to #2 above except the 2½" length dimensions were measured before and after the 3 hrs. at 110° C. vacuum-annealing schedule. Calculations were made using the following equation:

$$\text{Shrinkage During Annealing (in/in)} = \frac{\text{Length After Annealing} - \text{Length Before Annealing}}{\text{Length before annealing}}$$

| | MOLD TEMPERATURE* | | | | | | |
|---|---|---|---|---|---|---|---|
| | 87° F. | 102° F. | 116° F. | 140° F. | 158° F. | 181° F. | 194° F. |
| Linear Shrinkage During Annealing, (in/in) | $2.047 \times 10^{-3} \pm 3.84 \times 10^{-4}$ | $2.044 \times 10^{-3} \pm 3.87 \times 10^{-4}$ | $1.591 \times 10^{-3} \pm 8.90 \times 10^{-4}$ | $1.998 \times 10^{-3} \pm 3.01 \times 10^{-4}$ | $0.409 \times 10^{-3} \pm 6.09 \times 10^{-4}$ | $0.451 \times 10^{-3} \pm 4.08 \times 10^{-4}$ | $0.246 \times 10^{-3} \pm 4.81 \times 10^{-4}$ |

NOTES:
Shrinkage in 2½" length dimension average of lengths on right and left side of gate, before and after 3 hours at 110° C./vacuum annealing treatment.

$$\text{Linear shrinkage during annealing (in/in)} = \frac{\text{Length After Annealing} - \text{Length Before Annealing}}{\text{Length Before Annealing}}$$

*Measured

TABLE 6

PGA "ANNEALED" PROPERTIES IN FLEXURAL 3-POINT BENDING

"Annealed" Flexural Properties: identical to #3 above except samples were annealed under vacuum for 3 hours at 110° C. and allowed to cool overnight in the dry locker prior to testing.

| | MOLD TEMPERATURE* | | | | | | |
|---|---|---|---|---|---|---|---|
| | 87° F. | 102° F. | 116° F. | 140° F. | 158° F. | 181° F. | 194° F. |
| Flexural Modulus, (psi) | $1.07 \times 10^6$ ±43,700 | $1.04 \times 10^6$ ±29,500 | $1.06 \times 10^6$ ±23,600 | $1.10 \times 10^6$ ±32,200 | $1.11 \times 10^6$ ±29,600 | $1.13 \times 10^6$ ±11,700 | $1.10 \times 10^6$ ±6,950 |
| Ultimate Strength, (psi) | 31,300 ±755 | 30,900 ±538 | 31,700 ±471 | 32,300 ±446 | 32,500 ±665 | 33,000 ±209 | 32,300 ±318 |
| Ultimate Strain, (%) | 5.50 ±0.19 | 5.70 ±0.07 | 5.60 ±0.18 | 5.55 ±0.04 | 5.73 ±0.24 | 5.66 ±0.12 | 5.79 ±0.16 |

NOTES:
Molded samples were annealed under vacuum for 3 hrs. at 110° C. then allowed to cool overnight in the dry locker prior to testing.
2" span
0.2 in/min crosshead speed
5.0 in/min chart speed
100 lb. full scale load
ASTM #D-790 procedure
*Measured

II. Characterization of Injection-Molded Polyglycolic Acid Ligating Clips

Injection-molded polyglycolic acid (PGA ligating clips were characterized for dimensional stability. The results indicate much improved dimensional stability utilizing a higher mold temperature.

An unacceptable breakage rate upon closure (approximately 30%) persisted despite the mold modifications to eliminate interference. In reducing the overall interference, sacrifices were made in initial clip clamping force to an unacceptable level of about 5 lbs.

Recommendations to improve the breakage rate and the clamping force are to structurally change the clip design and to utilize a higher mold temperature to minimize dimensional changes during subsequent annealing. A higher mold temperature also allows the clips to be annealed with minimal fixturing.

A. Process Description

Approximately 300 samples of a ligating clip were injection molded from PGA using the conditions listed in Table 7. While sinking was not apparent, flash problems persisted. The flash problem can be minimized by using a hydraulic molding machine with the proper control on the injection profile.

The samples were zylene washed and overnight vacuum dried at room temperature. They were then annealed free-standing for 3 hours at 110° C. under vacuum, degated, deflashed and packaged for sterilization.

B. Dimensional Change Characterization

Prior to annealing, the overall length of twenty clips was measured and each clip was uniquely identified. The lengths were taken again after annealing.

The dimensional changes in overall length for the above procedure are shown in Tables 8 to 10 with the higher mold temperature to limit the dimensional changes during annealing, an overall consistent shrinkage of approximately 0.0012 inch from the original 0.369 inch length was observed during the annealing process. This result may be contrasted to a 0.010 inch shrinkage on cold molded samples. An approximately 90% improvement in shrinkage is obtained by utilizing the higher mold temperature.

Radiation sterilization of 2.5 Mrads created no detectable dimensional changes while ETO sterilization resulted in an average overall shrinkage of 0.0007 inch, but not with consistency. Within the standard deviation of the data, the shrinkage during ETO sterilization was insignificant.

The in-vitro results of part II are shown in the Tables 11 and 12.

TABLE 7

Process Conditions Utilized For Injection-Molded Characterization

| | |
|---|---|
| MATERIAL: | PGA |
| MACHINE: | Dynacast Mark MK-2 Serial #168-81 Plunger Type Pneumatic Injection - Molding Machine |
| TEMPERATURES: | Heating Chamber: 470° F. Hot Runner Block: 475° F. Mold: 225° F./225° F.: Front/Back |
| TIMES: | Initial Injection: 2 sec. Overall Injection: 5 sec. Overall Cycle: 40 sec. |
| Injection Pressure: | 50 psi (max) |
| Injection Speed: | 2 sec. (slow) |

TABLE 8

Dimensional Length Changes Of Clips On Annealing

| Lot No. | | Overall Length (inches) Prior to Annealing $L_0$ | Overall Length (inches) After Annealing $L_1$ | % Change | Difference in Length ($L_0 - L_1$) | Average Difference ($L_0 - L_1$) |
|---|---|---|---|---|---|---|
| A. | Average of 10 Samples | 0.3697 | 0.3686 | −0.2970% | .0011 | |
| | Deviation | ±0.0015 | ±0.0011 | ±0.1652 | | .0012 |
| B. | Average of 10 Samples | 0.3689 | 0.3676 | −0.3522% | .0013 | |
| | Deviation | ±0.0010 | ±0.0008 | ±0.1303 | | |

TABLE 9

Dimensional Length Changes of Clips on Sterilization Overall Length (inches)

| Lot No. | | After Annealing and prior to Sterilization+ | Sterilization Used | After Sterilization | % Change |
|---|---|---|---|---|---|
| A. | Average of 10 Samples | 0.3686 | ETO | 0.3679 (9 samples) | −0.1507%* |
| | Deviation | ±0.0011 | | ±0.0011 | ±0.1430 |
| B. | Average of 10 Samples | 0.3676 | 2.5 Mrad | 0.3676 | 0.0000% |
| | Deviation | ±0.0008 | | ±0.0008 | |

+From Table 8
*7 samples

TABLE 10

Dimensional Length Changes Of Clips On Crimping Overall Length (inches)

| Lot No. | | After Annealing & Sterilization+ | % Change | After Closure on Silastic ® | % Change |
|---|---|---|---|---|---|
| A. | Average of 9 Samples | 0.3679 | −0.1507%* | 0.3706* | 0.8168%* |
| | Deviation | ±0.0011 | ±0.1430 | ±0.0005 | ±0.3157 |
| B. | Average of 10 Samples | 0.3676 | 0.0000% | 0.3710* | 0.8942* |
| | Deviation | ±0.0008 | | ±0.0008 | ±0.3772 |

+From Table 9
*7 samples

TABLE 11

In-Vitro Opening (Pull-apart) Force of Medium J-Clip

| Lot No. | No. of Samples | No. Of Days in Buffer | Pull-Apart Force (Average) | Failure Mode |
|---|---|---|---|---|
| A. | | ETO Sterilized | | |
| 1. | 7 | 0 (Initial) | 5.34 ± 2.03 lb. | Teeth Shear Smooth |

TABLE 11-continued

In-Vitro Opening (Pull-apart) Force of Medium J-Clip

| Lot No. | No. of Samples | No. Of Days in Buffer | Pull-Apart Force (Average) | Failure Mode |
|---|---|---|---|---|
| 2. | 5 | 1 Day | 3.05 ± 0.95 lb. | Teeth Shear Smooth |
| 3. | 4 | 3 Days | 3.72 ± 0.31 lb. | Teeth Shear Smooth |
| 4. | 4 | 5 Days | 3.01 ± 1.81 lb. | Teeth Shear Smooth |
| 5. | 4 | 7 Days | 0.45 ± 0.10 lb. | Crescent Ear Broke |
| 6. | 4 | 10 Days | All opened prior to testing | Crescent Ear Broke |
| B. | | 2.5 Mrad Sterilized | | |
| 1. | 7 | 0 (Initial) | 5.04 ± 2.64 lb. | Teeth Shear Smooth |
| 2. | 5 | 1 Day | 2.11 ± 1.61 lb. | Teeth Shear Smooth |
| 3. | 5 | 3 Days | 1.55 ± 0.33 lb. | Teeth Shear Smooth |
| 4. | 4 | 5 Days | 0.61 ± 0.32 lb. | Crescent Ear Broke |
| 5. | 5 | 7 Days | 2 Samples opened prior to testing: 3 Samples crumbled in hands | |
| 6. | 5 | 10 Days | All opened prior to testing, crumbly | |

NOTE:
Clips were annealed and either ETO or 2.5 Mrad sterilized and applied to 0.058" × 0.077" SILASTIC ® (Dow Corning Co., U.S.A.) tubing to the full engagement of the teeth, immersed in pH 6.09 buffer @ 39° C. Pull-apart force measured at the applicator studs.

TABLE 12

In-Vitro Dynamic Pulse (Leak) Test of Medium j-Clip

| Lot No. | Sample No. | No. of Days to Leakage | Failure Mode |
|---|---|---|---|
| A. | ETO Sterilized | | |
| | 2 & 3 | 9 days | Crescent Ear Broke |
| | 4 to 6 | 10 days | Crescent Ear Broke |
| B. | 2.5 Mrad Cobalt-60 Sterilized | | |
| | 2. | 7 days | Crescent Ear Broke |
| | 3 to 6 | 8 days | Crescent Ear Broke |

NOTE:
Clips were annealed, either ETO or 2.5 Mrad sterilized and applied to 0.058" × 0.077" SILASTIC ® tubing to the full engagement of the teeth, immersed in 6.09 pH buffer at 39° C. Periodically a 6 psi average pressure was applied to the tubing and tube ends observed for leakage.

What is claimed:

1. An improved process for manufacturing an annealed prosthetic device from a synthetic bioabsorbable polymer containing a glycolic acid ester linkage comprising placing a solid amount of the polymer in a molding machine; melting said polymer by subjecting it to a temperature of from about 240° to 255° C.; transporting the polymer melt to an orifice; injecting said melt from said orifice into a closed mold cavity; holding said polymer in said mold cavity; removing the molded prosthetic device from said cavity; and annealing said device, the improvement comprising holding said polymer in said mold cavity for less than about one minute at a temperature from above 70° to about 90° C. whereby a dimensional change of said device during the annealing step is less than about 0.48 percent.

2. A process of claim 1 whereby the dimensional change is more than about 0.13 percent.

3. A process of claim 1 whereby the dimensional change is less than 0.48 and more than about 0.13 percent.

4. A process of claim 1 or 2 or 3 comprising annealing and then sterilizing said molded prosthetic device.

* * * * *